US010037672B1

(12) United States Patent
Abraham et al.

(10) Patent No.: US 10,037,672 B1
(45) Date of Patent: Jul. 31, 2018

(54) SMART GARMENTS THAT IDENTIFY USER CHANGES

(71) Applicant: International Business Machines Corporation, Armonk, NY (US)

(72) Inventors: Subil M. Abraham, Lewisville, TX (US); Marco A. Benavides, Dallas, TX (US); Diana P. Cabrera, Flower Mound, TX (US); Stephanie De La Fuente, Lewisville, TX (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 15/473,263

(22) Filed: Mar. 29, 2017

(51) Int. Cl.
| | |
|---|---|
| *G08C 19/22* | (2006.01) |
| *G08B 21/04* | (2006.01) |
| *A61B 5/00* | (2006.01) |
| *A61B 5/0205* | (2006.01) |
| *A61B 5/08* | (2006.01) |
| *A61B 5/021* | (2006.01) |
| *A61B 5/024* | (2006.01) |

(52) U.S. Cl.
CPC ........ *G08B 21/0453* (2013.01); *A61B 5/0008* (2013.01); *A61B 5/02055* (2013.01); *A61B 5/6804* (2013.01); *A61B 5/021* (2013.01); *A61B 5/024* (2013.01); *A61B 5/0816* (2013.01); *A61B 5/4266* (2013.01)

(58) Field of Classification Search
CPC ... A61B 5/6804; A61B 5/6805; A61B 5/7275; G08B 21/0453; G06Q 30/0631
USPC ..... 340/573.1–573.4; 705/26.5–26.7; 33/2 R
See application file for complete search history.

(56) References Cited

U.S. PATENT DOCUMENTS

| | | | |
|---|---|---|---|
| 8,429,025 | B2 | 4/2013 | Fries |
| 8,762,292 | B2 | 6/2014 | Bright et al. |
| 2013/0328783 | A1 | 12/2013 | Martin et al. |
| 2014/0052567 | A1 | 2/2014 | Bhardwaj et al. |
| 2014/0070957 | A1* | 3/2014 | Longinotti-Buitoni  A61B 5/02055 340/870.01 |

(Continued)

OTHER PUBLICATIONS

Konstantinos, P.T. et al., "Waist Circumference versus Other Obesity Indices for Prediction of Coronary Artery Disease in Essential Hypertension," Journal of the American College of Cardiology, vol. 65, No. 10, Mar. 17, 2015, p. A1403.
"Athos—Wearable Technology for Fitness," [online] Mad Apparel Inc. © 2013-2017 [retrieved Mar. 16, 2017], retrieved from the Internet: <https://www.liveathos.com/>, 4 pg.
Danvir, J. et al., "Design Features for a Jacket-Embedded Biomonitoring System," [online] IP.com Prior Art Database Technical Disclosure, No. IPCOM000137250D, Jun. 12, 2006, 3 pg.
"Stretch Sense," [online] StretchSense Limited © 2012-2017 [retrieved Mar. 2, 2017], retrieved from teh Internet: <https://www.stretchsense.com/>, 6 pg.

(Continued)

*Primary Examiner* — Joseph Feild
*Assistant Examiner* — Sharmin Akhter
(74) *Attorney, Agent, or Firm* — Cuenot, Forsythe & Kim, LLC

(57) ABSTRACT

Sensor data generated by at least a portion of a plurality of sensors integrated into a smart garment is received. The sensor data can indicate a level at which fabric of the smart garment is stretched when worn by a user. Based on the sensor data, at least one size change parameter indicating a change in a size of the user can be determined. Based on the size change parameter, whether a size of the smart garment is not suitable for the smart garment to be worn by the user can be determined. Responsive to determining that size of the smart garment is not suitable for the smart garment to be worn by the user, a notification can be output. The notification can indicate that the size of the smart garment is not suitable for the smart garment to be worn by the user.

20 Claims, 6 Drawing Sheets

(56) References Cited

U.S. PATENT DOCUMENTS

| | | |
|---|---|---|
| 2015/0026084 A1 | 1/2015 | Guo et al. |
| 2015/0145671 A1 | 5/2015 | Cohen et al. |
| 2015/0250420 A1 | 9/2015 | Longinotti-Buitoni et al. |
| 2015/0342266 A1* | 12/2015 | Cooper ................ A41B 11/00 705/26.7 |
| 2015/0342494 A1 | 12/2015 | Lou et al. |
| 2015/0370320 A1 | 12/2015 | Connor |
| 2016/0071397 A1 | 3/2016 | Logan et al. |
| 2016/0072802 A1 | 3/2016 | Hoyos |
| 2016/0080527 A1 | 3/2016 | Salem |
| 2016/0117749 A1 | 4/2016 | Desmarais et al. |
| 2016/0128632 A1 | 5/2016 | Wiebe et al. |
| 2016/0183835 A1 | 6/2016 | Varadan |

OTHER PUBLICATIONS

"LikeAGlove.me Jeans That Fit," [online] LikeAGlove.me © 2014-2016 [retrieved Mar. 16, 2017], retrieved from the Internet: <http://likeaglove.me/>, 11 pg.

Axisa, F. et al., "Smart Clothes for the Monitoring in Real Time and Conditions of Physiological, Emotional and Sensorial Reactions of Human," In Proc. of IEEE 25th Intl. Conf. of the Engineering in Medicine and Biology Society, Sep. 17, 2003, vol. 4, pp. 3744-3747.

* cited by examiner

600

```
┌─────────────────────────────────────────────────────────────────────────┐
│ Receive sensor data generated by at least a portion of a plurality of sensors integrated │
│    into a smart garment, the sensor data indicating at least one biometric parameter    │
│                       indicating a state of health of a user                            │
│                                          602                                            │
└─────────────────────────────────────────────────────────────────────────┘
                                           ↓
┌─────────────────────────────────────────────────────────────────────────┐
│           Determine, based on the sensor data, a risk of disease for the user           │
│                                          604                                            │
└─────────────────────────────────────────────────────────────────────────┘
                                           ↓
┌─────────────────────────────────────────────────────────────────────────┐
│        Determine whether the risk of the disease for the user exceeds a threshold value │
│                                          606                                            │
└─────────────────────────────────────────────────────────────────────────┘
                                           ↓
┌─────────────────────────────────────────────────────────────────────────┐
│ Responsive to determining that the risk of the disease for the user exceeds the threshold │
│         value, output a notification indicating the risk of the disease for the user    │
│                                          608                                            │
└─────────────────────────────────────────────────────────────────────────┘
```

Receive sensor data generated by at least a portion of a plurality of sensors integrated into a smart garment, the sensor data indicating at least one biometric parameter indicating a state of health of a user
702

↓

Determine, based on the sensor data, at least one health change parameter indicating at least one change in the state of health of the user
704

↓

Based on the at least one health change parameter indicating the at least one change in the state of health of the user, determine whether the at least one change in the state of health of the user exceeds a threshold value
706

↓

Responsive to determining that the at least one change in the state of health of the user exceeds the threshold value, output a notification indicating that the at least one change in the state of health of the user exceeds the threshold value
708

↓

Output another notification indicating a recommendation for the user to take at least one action to mitigate a health risk resulting from the change in the state of health of the user
710

FIG. 7

SMART GARMENTS THAT IDENTIFY USER CHANGES

BACKGROUND

The present invention relates to smart fabrics and, more particularly, the use of smart fabrics in smart garments.

Smart fabrics are fabrics that include electronic components. Smart fabrics can perform tasks that traditional fabrics do not. For example, from an aesthetic perspective, smart fabrics can be illuminated and/or change color. Smart fabrics also have been developed for protective clothing to guard against extreme environmental hazards like radiation and the effects of space travel. The health and beauty industry also is taking advantage of innovations such as drug-releasing medical fabrics, and fabrics that include moisturizer, perfume, and anti-aging properties.

SUMMARY

A method includes receiving first sensor data generated by at least a first portion of a plurality of sensors integrated into a smart garment, the first sensor data indicating a level at which fabric of the smart garment is stretched when worn by a user. The method also can include determining, using a processor, based on the first sensor data, at least one size change parameter indicating at least one change in a size of the user. The method also can include, based on the at least one size change parameter indicating the at least one change in the size of the user, determining whether a size of the smart garment is not suitable for the smart garment to be worn by the user. The method also can include, responsive to determining that size of the smart garment is not suitable for the garment to be worn by the user, outputting a first notification indicating that the size of the smart garment is not suitable for the smart garment to be worn by the user.

A system includes a processor programmed to initiate executable operations. The executable operations include receiving first sensor data generated by at least a first portion of a plurality of sensors integrated into a smart garment, the first sensor data indicating a level at which fabric of the smart garment is stretched when worn by a user. The executable operations also can include determining, based on the first sensor data, at least one size change parameter indicating at least one change in a size of the user. The executable operations also can include, based on the at least one size change parameter indicating the at least one change in the size of the user, determining whether a size of the smart garment is not suitable for the smart garment to be worn by the user. The executable operations also can include, responsive to determining that size of the smart garment is not suitable for the garment to be worn by the user, outputting a first notification indicating that the size of the smart garment is not suitable for the smart garment to be worn by the user.

A computer program includes a computer readable storage medium having program code stored thereon. The program code is executable by a processor to perform a method. The method includes receiving, by the processor, first sensor data generated by at least a first portion of a plurality of sensors integrated into a smart garment, the first sensor data indicating a level at which fabric of the smart garment is stretched when worn by a user. The method also can include determining, by the processor, based on the first sensor data, at least one size change parameter indicating at least one change in a size of the user. The method also can include, based on the at least one size change parameter indicating the at least one change in the size of the user, determining, by the processor, whether a size of the smart garment is not suitable for the smart garment to be worn by the user. The method also can include, responsive to determining that size of the smart garment is not suitable for the garment to be worn by the user, outputting, by the processor, a first notification indicating that the size of the smart garment is not suitable for the smart garment to be worn by the user.

BRIEF DESCRIPTION OF THE DRAWINGS

FIG. 6 is a flow chart illustrating an example of a method of outputting a notification regarding a risk of disease for a user.

FIG. 7 is a flow chart illustrating an example of a method of outputting a notification regarding a change in the state of health of a user.

DETAILED DESCRIPTION

Figure 1:
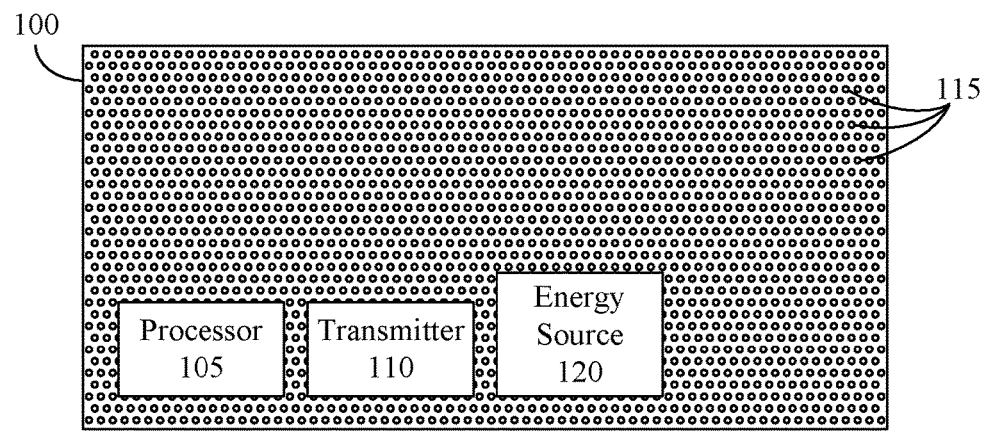
FIG. 1 is a pictorial diagram illustrating an example of a smart fabric.

This disclosure relates to smart fabrics and, more particularly, the use of smart fabrics in smart garments. In accordance with the inventive arrangements disclosed herein, a smart garment can include a plurality of sensors that generate sensor data. The sensor data can include tension data representing tension, and thus stretch, in the smart garment. The sensor data can be analyzed and, based on the analyses, any of a variety of determinations can be made about a user who is wearing the smart garment. For example, a determination can be made as to whether a size of the smart garment is suitable for the user. If not, a notification can be output to indicate to the user that the size is not suitable for the user. Further, the notification can indicate an appropriate size that would be suitable for the user and/or a particular garment having a size that is suitable for the user.

The sensor data further can include biometric parameters representing a state of health of the user. Based on the sensor data, determinations regarding the user's health can be made. Based on such determinations, any of a variety of notifications can be communicated to the user and/or a care giver of the user. By way of example, the notifications can provide recommendations to seek medical attention, to rest, to exercise, and so on. In a further example, based on the sensor data, a determination of whether the user has a risk, greater than a threshold value, of disease. The notifications can indicate such risk, and provide recommendations to mitigate the risk.

Several definitions that apply throughout this document now will be presented.

As defined herein, the term "smart garment" means a garment made, at least in part, of smart fabric.

As defined herein, the term "smart fabric" means a fabric that includes at least at least one electronic component.

As defined herein, the term "size" means a physical dimension.

As defined herein, the term "suitable" means appropriate for an intended purpose.

As defined herein, the term "client device" means a processing system including at least one processor and memory that requests shared services from a server, and with which a user directly interacts. Examples of a client device include, but are not limited to, a workstation, a desktop computer, a mobile computer, a laptop computer, a netbook computer, a tablet computer, a smart phone, a personal digital assistant, a smart watch, smart glasses, a gaming device, a set-top box, a smart television and the like. Network infrastructure, such as routers, firewalls, switches, access points and the like, are not client devices as the term "client device" is defined herein.

As defined herein, the term "server" means a processing system including at least one processor and memory that shares services one or more other systems and/or client devices.

As defined herein, the term "sensor" means a device that detects or measures a physical property and outputs corresponding data.

As defined herein, the term "processor" means at least one hardware circuit (e.g., an integrated circuit) configured to carry out instructions contained in program code. Examples of a processor include, but are not limited to, a central processing unit (CPU), an array processor, a vector processor, a digital signal processor (DSP), a field-programmable gate array (FPGA), a programmable logic array (PLA), an application specific integrated circuit (ASIC), programmable logic circuitry, and a controller.

As defined herein, the term "responsive to" means responding or reacting readily to an action or event. Thus, if a second action is performed "responsive to" a first action, there is a causal relationship between an occurrence of the first action and an occurrence of the second action, and the term "responsive to" indicates such causal relationship.

As defined herein, the term "computer readable storage medium" means a storage medium that contains or stores program code for use by or in connection with an instruction execution system, apparatus, or device. As defined herein, a "computer readable storage medium" is not a transitory, propagating signal per se.

As defined herein, the term "output" means storing in memory elements, writing to display or other peripheral output device, sending or transmitting to another system, exporting, or similar operations.

As defined herein, the term "automatically" means without user intervention.

As defined herein, the term "user" means a person (i.e., a human being).

FIG. 1 is a pictorial diagram illustrating an example of a smart fabric 100. The smart fabric 100 can include a processor 105. The smart fabric 100 also can include an RF transmitter (hereinafter "transmitter") 110 configured to transmit RF signals. In one arrangement, the transmitter 110 can be a component of a transceiver that also includes an RF receiver, although the present arrangements are not limited in this regard. The smart fabric 100 also can include a plurality of sensors 115 integrated into the smart fabric 100.

The processor 105 can include a computer readable storage medium, for example an erasable programmable read-only memory (EPROM or Flash memory), in which computer program code is stored. The computer program code can be executed by the processor, as will be described. The processor 105 also can include an accelerometer that detects movement, and/or any other suitable sensors or measurement components. Further, the processor 105 can include a plurality of input/output (I/O) ports to connect the processor to other devices, such as the transmitter 110 and the plurality of sensors 115. In one arrangement, the transmitter 110 can be a component of the processor 105.

Each of the plurality of sensors 115 can be communicatively linked to the processor 105, and the processor 105 can be communicatively linked to the transmitter 110. Electrical conductors (not shown) can be integrated into the smart fabric 100 to provide communication links between the processor 105 and the transmitter 110 and sensors 115. The smart fabric 100 also can include an energy source 120 that provides power to the processor 105, transmitter 110 and, optionally, the sensors 115. The energy source 120 can include, for example, a battery, a solar cell, a piezo electric charger, an inductive power supply, and/or any other devices that generate and/or provide electricity. In the case that the energy source 120 is an inductive power supply, the inductive power supply can generate electricity in response to a magnetic field generated by an inductive charger, as is known to those of ordinary skill in the art. Power can be conveyed from the energy source 120 to the processor 105, transmitter 110 and, optionally, the sensors 115 via electrical conductors.

In one arrangement, the electrical conductors can be embedded in threads of the smart fabric 100, for example by spinning the electrical conductors into the threads. In another arrangement, the electrical conductors can be woven with the threads into the smart fabric 100. Further, the sensors 115 can be embedded into the threads of the smart fabric 100 when the threads are spun or can be embedded into the smart fabric 100 when the smart fabric 100 is woven from the threads. The processor 105 and transmitter 110 also can be embedded into the smart fabric 100 when the smart fabric 100 is woven from the threads, or can be attached to the smart fabric 100 after the smart fabric 100 is woven.

In another arrangement, the processor 105, transmitter 110 and sensors 115 can be embedded in a flexible material that is configured to be attached to fabric to form the smart fabric 100. For example, the flexible material can include a substrate into which the processor 105, transmitter 110, sensors 115 and conductors are embedded. The flexible material can include an adhesive on at least one side configured to attach the flexible material to the fabric. In illustration, the adhesive can be configured to be activated with heat and/or light to bond the flexible material to the fabric. In an arrangement in which the adhesive is heat activated, the processor 105, transmitter 110, sensors 115 and conductors can be configured to withstand the amount of activation heat without becoming damaged during the process of attaching the flexible material to the fabric.

The transmitter 110 can be configured to receive signals from the processor 105, encode the signals, modulate the signals, etc. to generate corresponding RF signals. For example, the transmitter 110 can generate RF signals in accordance with a suitable RF communication protocol, for example in accordance with one more IEEE 802-15 standards (e.g., Bluetooth®, Bluetooth® low energy (BLE), Zigbee®, and so on) and/or near field communication (NFC).

In one aspect, at least a portion of the sensors 115 can be tension sensors (e.g., piezoelectric tension sensors, which are known in the art) configured to output to the processor 105 respective signals corresponding to an amount of tension, and thus stretch, of the smart fabric 100. In a further arrangement, at least a portion of the sensors 115 can be thermal sensors configured to output to the processor 105 respective signals corresponding to a temperature of a user wearing the smart fabric 100. Also, at least a portion of the sensors 115 can be perspiration sensors (or moisture sensors) configured to output to the processor 105 respective signals corresponding to a level of perspiration (or moisture) of a user wearing the smart fabric 100. Further, at least a portion of the sensors 115 can be respiration sensors configured to output to the processor 105 respective signals corresponding to a level of respiration of a user wearing the smart fabric 100. In a further arrangement, at least a portion of the sensors 115 can be heart rate sensors configured to detect a heart rate of a user wearing the smart fabric 100.

Also, at least a portion of the sensors 115 can be blood pressure sensors configured to output to the processor 105 respective signals corresponding to a level of blood pressure of a user wearing the smart fabric 100. In illustration, a garment into which the smart fabric 100 is incorporated can include a blood pressure cuff. The processor 105 can actuate the blood pressure cuff to expand with a compressed gas (e.g., air), and then slowly decompress. A portion of the sensors 115 can be configured to detect a systolic value and a diastolic value of the user's pulse.

In addition, at least a portion of the sensors 115 can be can be capacitive sensors configured to output to the processor 105 respective signals indicating whether the smart fabric 100 is being worn. For example, such sensors can be configured to detect and indicate a proximity of the sensors 115 to biological tissue. For example, when a garment made of the smart fabric 100 is worn, one or more sensors 115 may be placed proximate to a user's skin (e.g., within 0.5 mm, 1 mm, 2 mm, 3 mm, 4 mm, 5 mm, etc.), and the signals can indicate such.

Still, other types of sensors 115 can be utilized, and the present arrangements are not limited in this regard. In one arrangement, more than one type of sensor 115 can be used. For example, the plurality of sensors 115 can include one or more of the previously described sensors 115 and/or one or more other types of sensors.

In one non-limiting arrangement, each sensor 115 also can include a radio frequency identifier (RFID) tag. Each RFID tag can include a computer readable storage medium, for example an erasable programmable read-only memory (EPROM or Flash memory), configured to store respective data for the sensor 115. The data can include a unique identifier for the respective sensor 115. In addition, each RFID tag also can include a receiver (or transceiver), a decoder, a power supply and a processor configured to detect an RF signal, decode the RF signal to identify data contained in the RF signal, and also store the data contained in the RF signal in the computer readable storage medium. The power supply can generate energy for the decoder and processor to operate from energy contained in the RF signal, as is known in the art. As will be described, the data contained in the RF signal can indicate in which component of a smart garment the sensor 115 is integrated.

Figure 2:
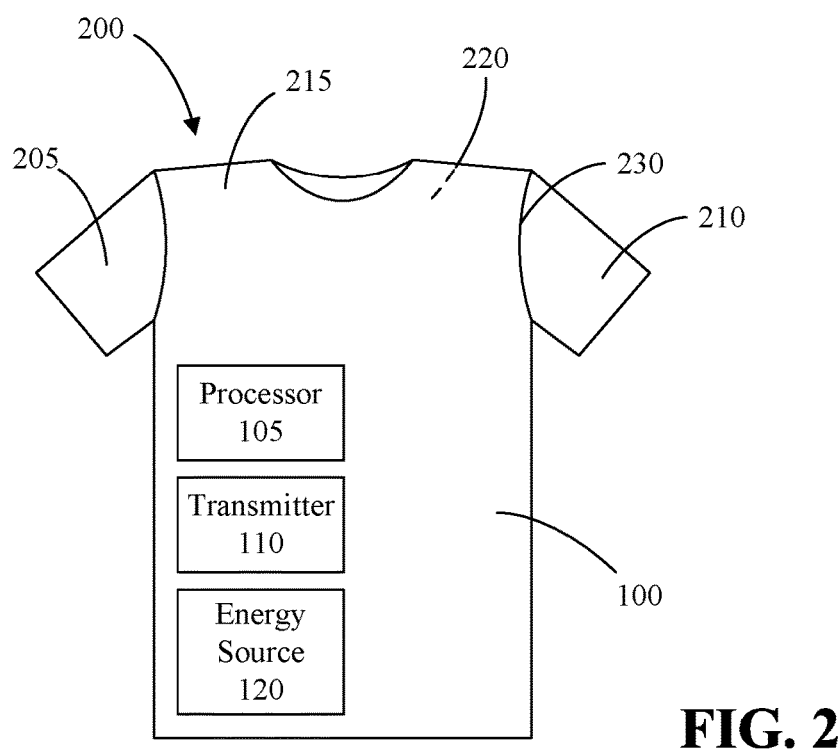
FIG. 2 is a pictorial diagram illustrating an example of a smart garment.

FIG. 2 is a pictorial diagram illustrating an example of a smart garment 200. The smart garment 200 can include the smart fabric 100 of FIG. 1. In illustration, the smart garment 200 can be made of the smart fabric 100. The smart garment 200 can be a shirt, a sweater, a jacket, pants, a skirt, a dress, a hospital gown, a shoe, or any other type of garment.

In one arrangement, different components 205, 210, 215, 220 of the smart garment 200 can be cut from the smart fabric 100, and perhaps one or more other smart fabrics (not shown) following a garment pattern, and the components 205-220 can be sewn together to create the smart garment 200. The processor 105, transmitter 110 and energy source 120 can be integrated into a respective portion of the smart fabric 100 used for any of the smart garment components 205-220, and the present arrangements are not limited in this regard.

During the cutting process, various electrical conductors may be cut. During the sewing process, electrical connections to the sensors 115 can be re-established by connecting ends respective ends of electrical conductors. For example, at a seam 230 where a sleeve 210 is connected to a front 215 and back 220 of the smart garment 200, there may be electrical conductors in the sleeve 210, front 215 and back 220 that have been cut, and the electrical conductors of the sleeve 210 can be attached to the electrical conductors of the front 215 and back 220 of the smart garment 200 to form continuous electrical connections between the processor 105 and the sensors 115. Since the sleeve 210, front 215 and back 220 may be cut from different portions of the smart fabric 100, the electrical path between the processor 105 and each sensor 115 in the sleeve 210 need not be the same electrical path that was between the processor 105 and each of such sensors 115 in the smart fabric 100 prior to the components 205-220 being cut from the smart fabric 100. The respective ends of the electrical conductors may be connected at the seam 230 by a person (e.g., a seamstress) while sewing the smart garment 200 or by a robot configured to perform such operation. The respective ends of the electrical conductors may be connected by soldering or welding the respective ends of the electrical conductors together, or using electrical connectors. The other components 205-220 of the smart garment 200 can be sewn, and respective ends of electrical conductors can be connected, in a similar manner.

At some point during manufacturing of the smart garment 200, for example after the components 205-220 have been cut from the smart fabric 100, each of the components 205-220 can be scanned using an RF scanner, such as an RFID scanner. The RFID scanner can be configured to scan each component 205-220 and communicate to the RFID tags of the respective sensors 115 data indicating in which component 205-220, and where in the component 205-220, the sensors 115 are integrated. For example, for a lower part of the sleeve 210, a person or automated system can enter data indicating "lower left sleeve" into the RFID scanner, and scan the portion of the smart fabric 100 in the lower part of the sleeve 210 with the RFID scanner. The RFID tag in each sensor 115 of the lower part of the sleeve 210 can detect the RF signal emitted by the RFID scanner, and store the data indicating "lower left sleeve" into the respective computer readable storage medium. The process can be repeated for each of the components 205-220, as well as different portions of the components 205-220.

At some point after the electrical conductors have been connected, and perhaps after the smart garment 200 is sewn, a person or automated system can provide to the processor 105 information identifying the smart garment 200, such as a garment model number, serial number, size, color style, etc. For example, the person or automated system can scan the processor with an RF device, such as an RFID scanner, which can communicate to the processor the data containing the identifying information. The processor 105 can store the data in the computer readable storage medium of the processor 105. In this regard, responsive to the processor 105 receiving, via a receiver (e.g., an RF receiver that is a component of a transceiver that includes the transmitter 110), an RF signal containing identifying information, the processor 105 can store data.

Further, the person or automated system can initiate the processor 105 to execute the program code of the processor 105 to retrieve baseline sensor data from the sensors 115 integrated into various the components 205-220 of the smart garment 200 to generate baseline measurements for the sensors 115. The processor can receive energy from the energy source 120, or energy contained in a received RF signal, to generate the baseline measurements, and can receive the baseline sensor data via the aforementioned electrical conductors. A person or automated system can initiate the processor 105 to retrieve the baseline sensor data by depressing a button integrated into the processor, or scanning the processor with an RF device. In the case an RF device is used, responsive to receiving an RF signal containing particular data, the processor 105 can execute computer program code that causes the processor to poll each of the sensors 115 integrated into the various the components 205-220 of the smart garment 200.

The processor 105 can store data received from each sensor 115 in one or more data tables within the computer readable storage medium of the processor 105. The data retrieved from each sensor 115 can identify the specific sensor 115, indicate in which component 205-220 respective sensor 115 is integrated, and indicate a portion of the component 205-220 in which the sensor 115 is integrated. The data also can include a baseline sensor reading, for example a tension reading, temperature reading, moisture reading, etc. detected by the respective sensor 115. For each respective sensor 115, the processor 105 can create an association between the sensor identifier, the baseline sensor reading and the data indicating in which component 205-220, and in which portion of the components 205-220, the sensor is integrated. As each sensor 115 is polled by the processor 105, the respective sensor 115 can use energy contained in the polling signal to perform the baseline sensor reading and communicate the various data to the processor 105. Once the baseline sensor measurements are stored by the processor 105, the smart garment 200 is ready for packaging and sale. Of course, tags, etc. can be added to the smart garment 200 if this is desired.

The processor 105 can be configured to monitor sensor data generated by the sensors 115, and process the sensor data to determine if the smart garment 200 is being worn by a user. For example, responsive to the processor detecting movement (e.g., using an accelerometer) or detecting a particular RF signal, the processor 105 can initiate execution of program code to poll the sensors 115 to receive sensor data. When a sensor 115 is proximate to a user's biological tissue (e.g., skin), the sensor 115 can measure a value of capacitance that is different from a value of capacitance measured when the sensor 115 is not proximate to the user's biological tissue (e.g., different from the baseline sensor measurement). Thus, the processor 105 can be configured to determine that the sensor 115 is proximate to biological tissue if the sensor 115 generates a sensor value within a particular range of sensor values, which can be predetermined.

Responsive to the processor 105 receiving sensor data from a threshold number of the sensors 115 indicating that each of those sensors 115 is proximate to biological tissue, the processor 105 can determine that the smart garment 200 is being worn by a user. In response, the processor 105 can monitor signals from other sensors 115 that indicate other parameters, such as those previously described. The processor 105 can process such signals to determine the other parameters. Further, the processor 105 can store the parameters locally, within the processor 105 and/or a computer readable storage medium (not shown) communicatively linked to the processor 105, and/or communicate the parameters to one or more other systems, as will be described.

Figure 3:
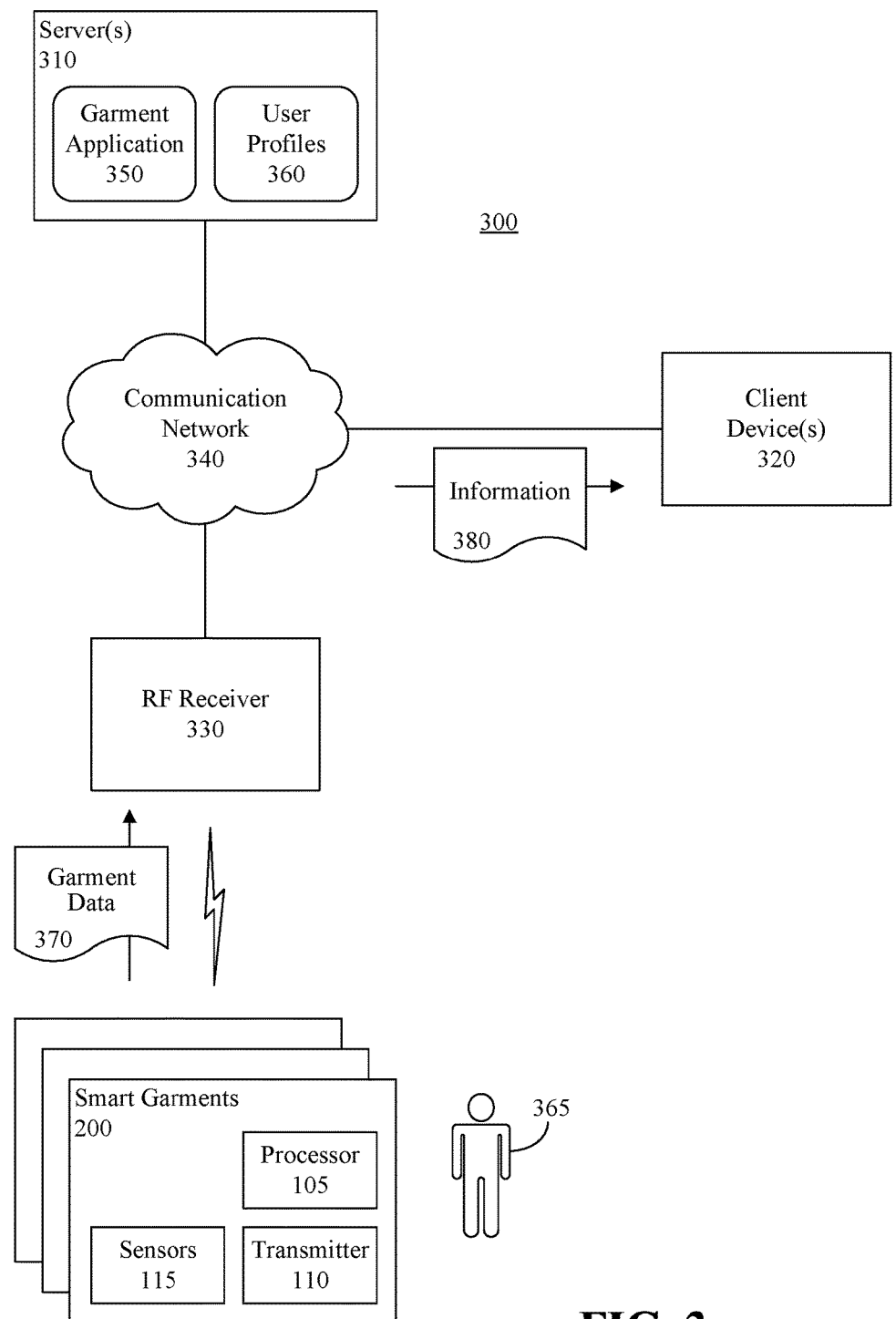
FIG. 3 is a block diagram illustrating an example of a data processing environment.

FIG. 3 is a block diagram illustrating an example of a data processing environment (hereinafter "environment") 300. The environment 300 can include the smart garment 200 of FIG. 2, and may include one or more additional smart garments. The environment 300 also can include one or more servers 310, one or more client devices 320 and one or more receivers (e.g., transceivers) 330. The client device(s) 320 and RF receiver(s) 330 can be communicatively liked to the server(s) 310 via a communication network 340.

The communication network 340 is the medium used to provide communications links between various devices and systems connected together within the environment 300. The communication network 340 may include connections, such as wire, wireless communication links, or fiber optic cables. The communication network 340 can be implemented as, or include, any of a variety of different communication technologies such as a WAN, a LAN, a wireless network, a mobile network, a Virtual Private Network (VPN), the Internet, the Public Switched Telephone Network (PSTN), or similar technologies.

The server 310 can include a garment application 350 executable by one or more processors of the server 310, and store user profiles 360 for various users, including a user 365 of the smart garment 200 (e.g., a person who wears the smart garment 200). The server 310 can store the user profiles 360 locally or on one or more computer-readable storage devices communicatively linked to the server 310. The garment application 350 can host a user interface in which users interact with the server 310 via the client device(s) 320, or interface with one or more mobile application via which the users interact with the server 310.

Each RF receiver 330 can be configured to send and receive RF signals communicated in accordance with one more suitable RF communication protocols. For example, the RF receiver(s) 330 can communicate in accordance with one or more of the IEEE 802-15 communication standards and/or near field communication (NFC). The RF receiver(s) 330 can receive garment data 370 from the transmitter 110 of the smart garment 200, as well as receive garment data from transmitters from other smart garments. The garment data 370 can include data generated by the sensors 115. By way of example, at least one RF receiver 330 can be located in a residence of the user 365, in a medical care facility (e.g., a hospital, a doctor's office, a diagnostic center, etc.). In one aspect, multiple receivers 325 can be located in the user's place of residence and/or multiple receivers 325 can be located in a medical care facility. For instance, an RF receiver 330 can be located in a room of user's place of residence, an RF receiver 330 can be located in a room or area of the medical care facility, and so on. The client device(s) 320 and RF receiver(s) 330 also can be communicatively linked to the server(s) 310 via the communication network 340.

The garment application 350 can receive sensor data generated by the sensors 115 of the smart garments 200 as garment data 370. The garment application 350 can receive the garment data 370 via the RF receiver(s) 330 and the communication network 340. In response to receiving the garment data 370, the garment application 350 can process the garment data 370 and, based on such processing, make any of a myriad of determinations regarding the user 365 and/or the smart garment 200. Further, the garment application 350 can communicate to the client device(s) 320 information 380 indicating the garment data 370, results of the determinations regarding the user 365 based on the garment data 370 and/or any other information.

In one arrangement, the garment application 350 can receive the garment data 370 each time a smart garment 200 is worn by a user 365. The garment data 370 for each instance of the smart garment 200 being worn can indicate a level of stretch in one or more portions of the smart garment 200. The garment application 350 can compare the garment data 370 from each instance of the smart garment 200 being worn by the user 365 to the garment data 370 generated from previous instances of the smart garment 200 being worn by the user 365. Based on such comparison the garment application 350 can determine at least one size change parameter indicating at least one change in a size of the user 365. Based on the size change parameter, the garment application 350 can determine whether a size of the smart garment 200 is not suitable for the smart garment 200 to be worn by the user 365 (e.g., the smart garment 200 is too small or too large for the user 365). Responsive to determining that size of the smart garment 200 is not suitable for the garment to be worn by the user 365, the garment application 350 can output an indication that the size of the smart garment is not suitable for the smart garment to be worn by the user 365. For example, the garment application 350 can output the indication in information 380 by communicating the information 380 to one or more client devices 320. The client device 320 can be a client device of the user 365 and/or a client device of a care giver of the user 365.

In another arrangement, the garment data 370 generated by a particular smart garment 200 can indicate whether a size of the smart garment 200 is not suitable for the smart garment 200 to be worn by the user 365. For example, rather than the garment application 350 comparing data generated by the sensors 115 for various instances of the smart garment 200 being worn, the processor 105 of the smart garment 200 can perform such comparisons to determine at least one size change parameter indicating at least one change in a size of the user 365, and include in the garment data 370 information indicating whether the size of the smart garment 200 is suitable for the smart garment 200 to be worn by the user 365. In such an arrangement, the processor 105 can communicate the garment data 370 to the garment application 350 which, in turn, can output information 380 based on the garment data 370. In a further arrangement, the processor 105 can communicate the garment data 370 directly to the client device(s) 320 via the RF receiver 330 and the communication network 340. In this regard, the processor 105 can output an indication that the size of the smart garment 200 is not suitable for the smart garment 200 to be worn by the user 365 by communicating the information 380 directly to the client device(s) 320.

The size of the smart garment 200 can be considered to be suitable to be worn by the user 365 if data indicating a stretch of the smart garment 200 when worn by the user 365 is below a threshold value, or is between a minimum threshold value and a maximum threshold value. Such data can be garment data 370 generated by sensors 115 in any portion of the smart garment 200, an average of garment data 370 generated by sensors 115 in a plurality of portions of the smart garment 200, and/or data generated by processing garment data 370 generated by sensors 115 in a plurality of portions of the smart garment 200.

In illustration, the garment application 350 (or the processor 105) can apply a weighting factor to the sensor data generated by the sensors 115 based on the locations of the sensors 115. The garment application 350 (or the processor 105) can specify the weighting factor. For example, the garment application 350 can specify a greater weight (e.g., a weighting value above a threshold value) to garment data 370 generated by sensors in a first portion of the smart garment 200 (e.g., in a portion of the smart garment 200 that covers a user's abdomen) and specify a lesser weight (e.g., a weighting value below a threshold value) to garment data 370 generated by sensors in a second portion of the smart garment 200 (e.g., in a portion of the smart garment 200 that covers a user's bicep).

For example, the garment data 370 can include data generated by the sensors 115 indicating a level of stretch of the smart fabric from which the smart garment 200 is made. If the level of stretch is below a first threshold value, the garment application 350 can determine that the size of the smart garment 200 is too large for the user 365. If the level of stretch is above a second threshold value, the garment application 350 can determine that the size of the smart garment 200 is too small for the user 365. If the level of stretch is between the first threshold value and the second threshold value, the garment application 350 can determine that the size of the smart garment 200 is suitable for the user 365.

In one aspect of the present arrangements, the garment application 350 (or processor 105) can, based on the garment data 370, determine a garment size that is suitable for the user 365. In illustration, the garment data 370 can indicate a particular smart garment 200, a size of the smart garment 200, and a level of stretch in one or more portions of the smart garment 200 when the smart garment 200 is worn by the user 365. The garment application 350 (or processor 105) can, based on the size of the smart garment 200 and the level of stretch in one or more portions of the smart garment 200 when the smart garment 200 is worn by the user 365, determine a suitable size of the garment for the user. The garment application 350 (or processor 105) can indicate such suitable size in the information 380 communicated to the client device(s) 320. Such indication can be provided responsive to the garment application 350 (or processor 105) determining that size of the smart garment 200 is not suitable for the garment to be worn by the user 365.

In a further aspect of the present arrangements, the garment application 350 (or processor 105) can determine one or more other particular garments that are different from the smart garment 200. For example, the other garments can be different styles and/or different types from the smart garment 200, and may be different in size from the smart garment 200. Responsive to determining that size of the smart garment 200 is not suitable for the smart garment 200 to be worn by the user 365, the garment application 350 (or processor 105) can output an indication of a particular garment having a garment size that is suitable for the user 365 in the information 380 communicated to the client device(s) 320. Such indication can be provided responsive to the garment application 350 (or processor 105) determining that size of the smart garment 200 is not suitable for the garment to be worn by the user 365.

In other aspects of the present arrangements, the garment data 370 can include biometric parameters indicating a health of the user 365.

In illustration, one or more portions of the sensors 115 can be configured to measure biometric parameters of the user 365. The biometric parameters can include, but are not limited to, a body temperature of the user 365, a heart rate of the user 365, a respiration rate of the user 365, a level of perspiration rate of the user 365, a blood pressure of the user 365, a blood sugar level of the user 365, and so on. In such an arrangement, the smart garment 200 can include sensors 115 configured to detect body temperatures of the user 365, respiration rates of the user 365, perspiration rates (e.g., levels of body moisture) of the user 365, blood pressure of the user 365, blood sugar levels of the user 365, etc. In some arrangements, the smart garment 200 may include additional devices in addition to the sensors 115, transmitter 110 and processor 105. For example, the smart garment may include an inflatable cuff controllable by the processor 105 to inflate and deflate for blood pressure measurements in accordance with known blood pressure measurement techniques. In one aspect of the present arrangements, the smart garment 200 can be a gown worn by the user 365 while in a medical care facility.

The garment application 350 can analyze the biometric parameters and, based on such analysis, provide recommendations to the user 365 or a care giver of the user 365 in the information 380 communicated to the client device 320. For example, based on analyzing the biometric parameters, the garment application 350 can determine patterns in the biometric parameters (e.g., medical patterns). Based on the determined patterns, the garment application 350 can determine the recommendations. In illustration, the information 380 can include a recommendation for the user to visit a health care facility and/or a medical practitioner, a recommendation for the user to rest, a recommendation for the user to perform exercises, a recommendation for the user to take medication, and so on. In this regard, the information 380 can include recommendations for the user to take at least one action to improve the user's health.

Further, the garment application 350 can analyze the biometric parameters, as well as other parameters (e.g., determined size change parameters indicating weight gain or weight loss) and, based on such analysis, determine a risk of disease for the user 365. For example, the garment application 350 can determine a risk of the user 365 having one or more diseases. In another example, the garment application 350 can determine a risk that user 365 may contract one or more diseases. The garment application 350 also can determine whether any such risks exceed a threshold value. If so, the garment application 350 can generate one or more notifications regarding such risks, and communicate the notifications to the client device(s) 320 in the information 380. The notifications can be presented to the user 365 or a care giver of the user 365.

By way of example, as noted, based on the sensor data the garment application 350 can determine size change parameters indicating a change in size of the user 365. The size change parameters can indicate a particular portion of the user's body that has changed in size, for example in the abdominal region. If the size of the abdominal region has increased, this can indicate a weight gain. The amount of tension measured by sensors 115 that detect tension, along with the size of the smart garment 200, can indicate a body mass index for the user 365, which the garment application 350 can determine based on processing the garment data 370. Based on the body mass index of the user 365 and various biometric parameters generated by the sensors 115, for example blood pressure, heart rate and/or respiration rate, the garment application 350 can determine a risk of the user 365 having a heart disease.

To perform the described analyses of the various parameters, the garment application 350 can interface with one or more medical databases, which may be components of the server(s) 310 or a components of external resources (not shown), and access medical data that correlates symptoms to diseases, health recommendations, etc. The garment application 350 can analyze the various parameters using the medical data to arrive at various medically related determinations described herein. Further, the garment application 350 can perform predictive analysis, which will be described herein, to predict symptoms indicated by various parameters. In illustration, an increase in the size of the user's abdominal region may be due to increased obesity, but may be due to other factors, for example pregnancy. Using predictive analysis, the garment application 350 can predict symptoms that cause the changes, and use such predictions when analyzing the various parameters to arrive at the various determinations.

Moreover, the garment application 350 can be configured to, based on the biometric parameters indicated in the garment data 370, determine at least one health change parameter indicating at least one change in the state of health of the user 365. For example, the garment application 350 can monitor, over time, various biometric parameters for the user 365 indicated in the garment data 370. Based on such monitoring, the garment application 350 can identify changes in the biometric parameters over time. Based on the at least one health change parameter indicating the at least one change in the state of health of the user 365, the garment application 350 can determine whether the at least one change in the state of health of the user exceeds a threshold value. If so, in response, the garment application 350 can output an indication that the at least one change in the state of health of the user 365 exceeds the threshold value, for example in the information 380 communicated to the client device(s) 320.

By way of example, at least a portion of the sensors 115 can be configured to detect a respiration rate and/or heart rate of the user 365 and communicate corresponding biometric parameters to the processor 105. The processor 105 can be configured to monitor and process such biometric parameters. Responsive to identifying, based on processing the biometric parameters, a change in the user's respiration rate and/or heart rate that exceeds a threshold value, for example within a predetermined period of time, the processor 105 can output an indication that the at least one change in the state of health of the user exceeds the threshold value. In one aspect, the processor 105 can output the indication in garment data 370 communicated to the garment application 350. In response, the garment application 350 can communicate information 380 to one or more client device(s) 320 alerting persons, who may or may not include the user 365, of the indication that the at least one change in the state of health of the user exceeds the threshold value. In another aspect, the processor 105 can communicate the information 380 directly to the client device(s) to alert persons, who may or may not include the user 365, of the indication that the at least one change in the state of health of the user exceeds the threshold value. It should be noted that the present arrangements are not limited to respiration rate and heart rate, and the above processes also can be applied to biometric parameters indicating the user's temperature, blood pressure, or any other biometric parameters the sensors 115 may detect.

In one arrangement, outputting the indication that the at least one change in the state of health of the user 365 exceeds the threshold value can include generating an alert. In illustration, information 380 communicated to the client device(s) 320 can include an alert. Moreover, an alert can be communicated to various other devices, for example output audio transducers (e.g., loudspeakers) configured to propagate audio alert signals, indication lights configured to propagate visual alert signals, and so on. Further, the information 380 can include recommendations for the user to take at least one action to improve the user's health. For example, the information 380 can include recommendations to take actions predicted to mitigate health risks resulting from the change in the state of health of the user 365. In illustration, if the user's heart rate is above a threshold level, the garment application 350 can generate a recommendation for the user to rest, to take medication and/or to seek medical attention. Still, the information 380 can include any of a myriad of recommendations based on the change in the state of health of the user 365, and the present arrangements are not limited in this regard.

The determination of the information 380 also can be based on any of a myriad of data from the user profiles 360 and other data. For example, the information can be based on the user profiles 360, environmental data, fabric and clothing data, and so on. The user profiles 360 can include user data including, but not limited to, name, age body measurements, biometric data, activity data (including physical activity), size and material preferences, clothing feedback, family health history (including likelihood of developing diseases), health history (including allergy history), etc. The environmental data can include weather data, allergen information (including allergy tracking, pollen count and pollen forecast), ambient temperature, etc. The fabric and clothing data can include material, dimensions, weight, thickness, color, density, state (dry, wet, stretching data etc.), clothing article identifier and/or serial number, and so on.

Figure 4:
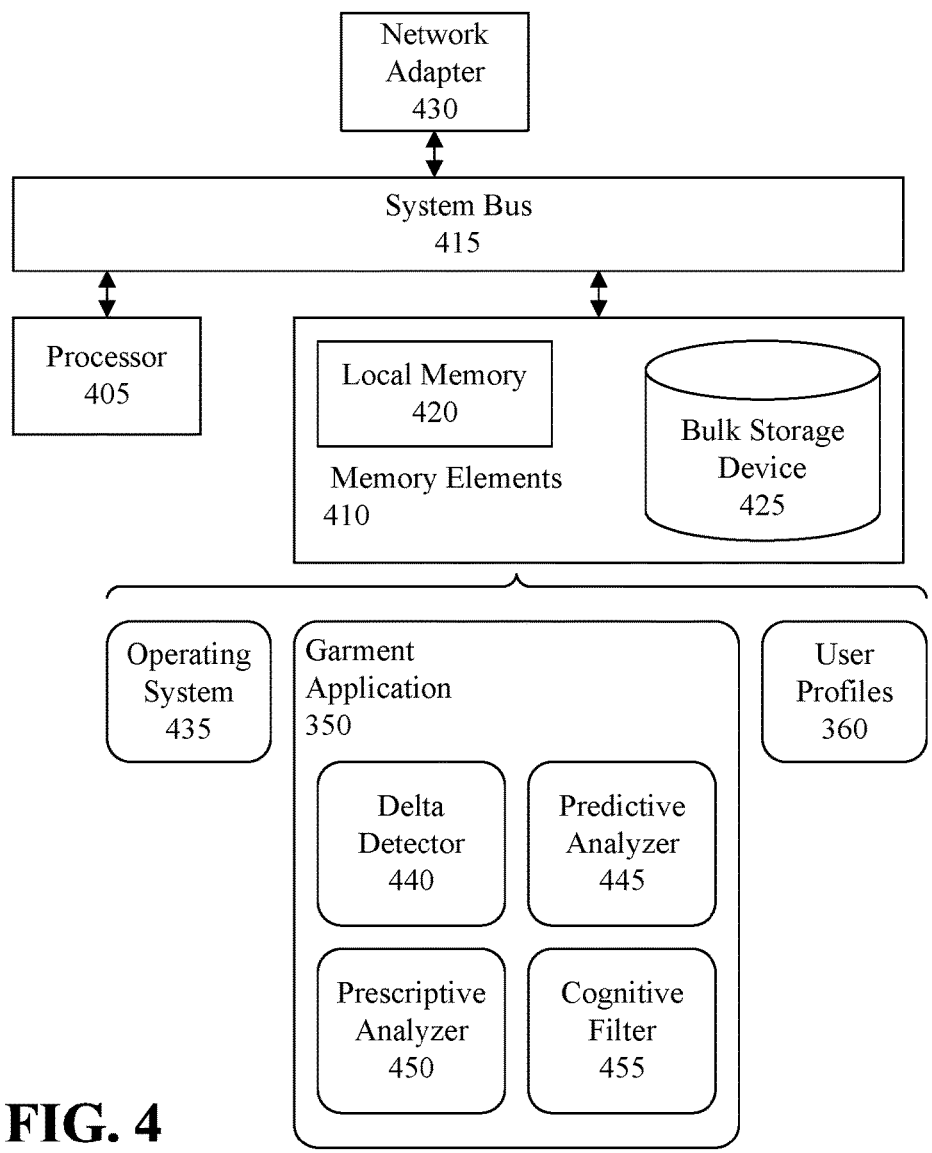
FIG. 4 is a block diagram illustrating example architecture for a server.

FIG. 4 is a block diagram illustrating example architecture for a server 310. The server 310 can include at least one processor 405 (e.g., a central processing unit) coupled to memory elements 410 through a system bus 415 or other suitable circuitry. As such, the server 310 can store program code within the memory elements 410. The processor 405 can execute the program code accessed from the memory elements 410 via the system bus 415. It should be appreciated that the server 310 can be implemented in the form of any system including a processor and memory that is capable of performing the functions and/or operations described within this specification.

The memory elements 410 can include one or more physical memory devices such as, for example, local memory 420 and one or more bulk storage devices 425. Local memory 420 refers to random access memory (RAM) or other non-persistent memory device(s) generally used during actual execution of the program code. The bulk storage device(s) 425 can be implemented as a hard disk drive (HDD), solid state drive (SSD), or other persistent data storage device. The server 310 also can include one or more cache memories (not shown) that provide temporary storage of at least some program code in order to reduce the number of times program code must be retrieved from the bulk storage device 425 during execution.

One or more network adapters 430 can be coupled to server 310 via the system bus 415 to enable the server 310 to become coupled to other systems, computer systems, remote printers, and/or remote storage devices through intervening private or public networks. Modems, cable modems, transceivers, and Ethernet cards are examples of different types of network adapters 430 that can be used with the server 310.

As pictured in FIG. 4, the memory elements 410 can store the components of the server 310, namely an operating system 435, the garment application 350 and the user profiles 360. Being implemented in the form of executable program code, the operating system 435 and the garment application 350 can be executed by the server 310 and, as such, can be considered part of the server 310. Moreover, the operating system 435, the garment application 350 and the user profiles 360 are functional data structures that impart functionality when employed as part of the server 310.

The garment application 350 can include various components, for example, a delta detector 440, a predictive analyzer 445, a prescriptive analyzer 450 and a cognitive filter 455. The delta detector 440, predictive analyzer 445, prescriptive analyzer 450 and a cognitive filter 455 also are functional data structures that impart functionality when employed as part of the server 310.

The delta detector 440 can, based various parameters generated by the sensors 115 of FIG. 3, detect and record changes in the states of smart garments 200 and/or biometric states of the user. Examples of the changes in state include, but are not limited to, stretching of the smart garment 200 when worn, body temperature changes of the user, heart rate changes of the user, perspiration rate changes of the user, blood pressure changes of the user, blood sugar level changes of the user, and so on. The delta detector 440 also can measure levels of changes in the states, and record such levels as delta values. Moreover, the delta detector 400 can record with the detected changes and the determined delta values an indication parameters indicating where on the smart garment 200 the sensors 115 are located that generated the sensor data used to determine the detected changes and the determined delta values. Such parameters can facilitate analysis of the sensor data. For example, a person who is exercising and sweating may sweat more profusely in certain areas, and those areas may be known to have a higher temperature and moisture than other areas during exercise. Accordingly, when analyzing the data, the garment application 350 can predict that the increased moisture and temperature in those areas are a result of exercising instead of a being due to a medical issue. In another example, if a person is walking in the rain, it is more likely that they will have moisture on their shoulders, chest area and back than other areas of the body. If, when analyzing the data, the garment application 350 detects a higher level of moisture in those areas, and the garment application 350 accesses data indicating rainy weather conditions, the garment application 350 can predict that the moisture is due to rain rather than being due to a medical issue.

As noted, the garment application 350 can detect different levels of tension (e.g., stretch) in different areas of the smart garment 200. Further, the delta detector 440 can detect a difference in tension, or stretch, between when the garment is worn and the garment is not worn, and record corresponding delta values for various regions of the smart garment 200. The delta detector 400 also can determine additional delta values representing the change in the tension over time, for example as the user gains or loses weight. The garment application 350 can analyze the various delta values to detect and learn about changes in the user's body over time. Such changes can be considered by the garment application 350 when performing various analyses, such as those previously described with respect to FIG. 3.

The predictive analyzer 445 can process sensor data received from the sensors 115 in the garment data 370 to help determine the previously described risk of disease. For example, the waist size of the user can be a parameter that is analyzed to predict accurately the user's risk of experiencing heart disease. As noted, however, a person's waist size can vary for various reasons, and the predictive analyzer 445 can process waist size parameters along with various other detected and/or generated parameters to predict a cause of the change in waist size. For example, delta values corresponding to tension around the waste can indicate in increase in waist size corresponding to pregnancy, rather than obesity. Using predictive analytics, the predictive analyzer 445 can identify such circumstance. The garment application 350 can use the results of the prediction when determine various medical analyses for the user, such as those previously described. Moreover, as the delta detector 440 generated delta values over time, the predictive analyzer 445 can update various predictions for the user.

The prescriptive analyzer 450 can determine various recommendations for the user based on the sensor data generated by the sensors 115, data generated by the delta detector 440, and data generated by the predictive analyzer 445. As noted, examples of such recommendations can include a recommendation to see a medical professional, a recommendation to increase or decrease levels of physical activity, etc. Other examples include a recommendation to increase or decrease caloric, nutritional or supplemental indicate, a recommendation to purchase clothing in a different size, recommendation to purchase clothing using a different fabric or material, etc. Because the user's data may change of time, the prescriptive analyzer 450 can update recommendations, but also may re-prescribe other recommendations that still are relevant to the user.

The cognitive filter 455 can implement cognitive analysis, which is known in the art, to track garment data 370 from various smart garments 200 worn or purchased by the user, and learn the user's clothing preferences. Further, the cognitive filter 455 can learn which sizes of clothing fit the user for various brands. For example, the user may wear size 4 in clothing from a first manufacturer, but wear size 6 in clothing from a second manufacturer, and the cognitive filter 455 can learn and store corresponding data. Still, the cognitive filter 455 can perform various other types of cognitive analysis, and the present arrangements are not limited in this regard.

Figure 5:
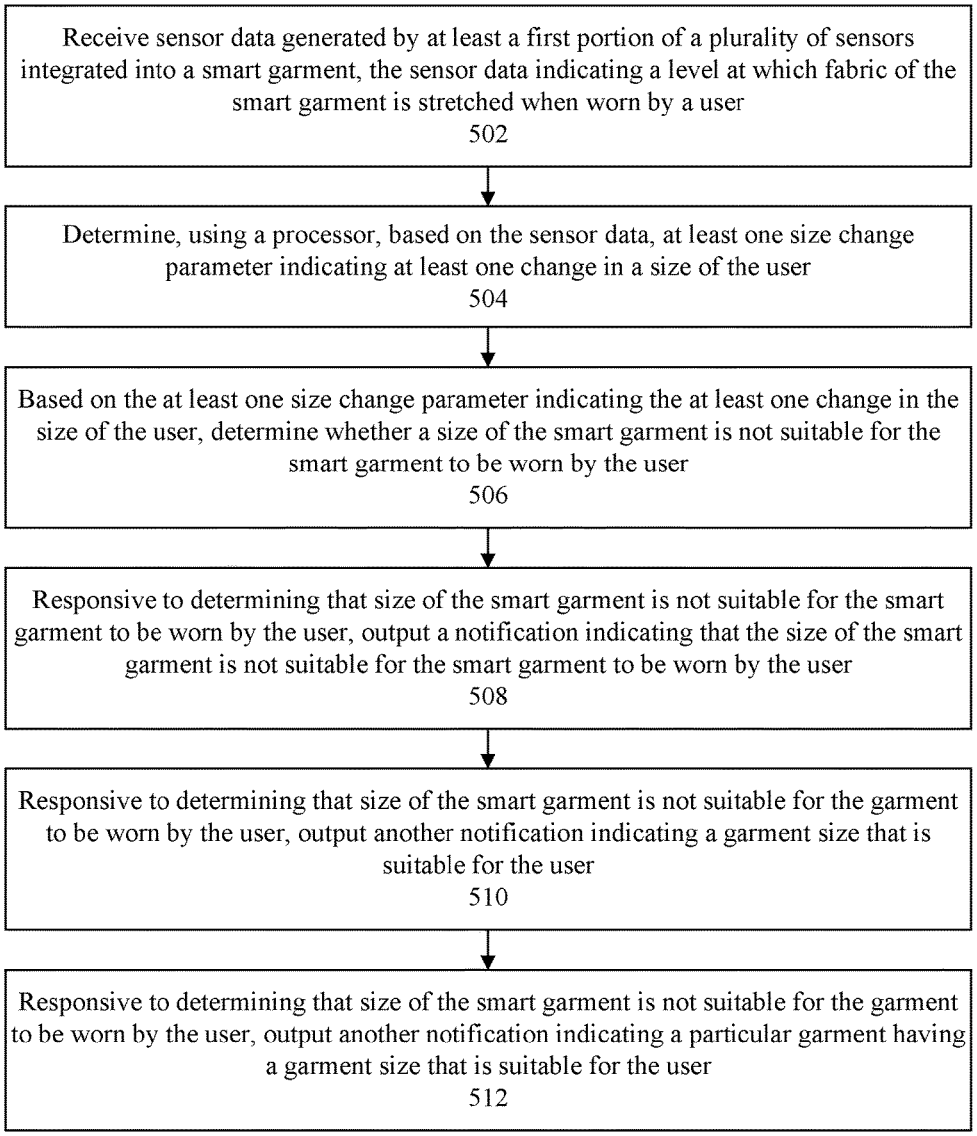
FIG. 5 is a flow chart illustrating an example of a method of outputting a notification regarding a size of a smart garment.

FIG. 5 is a flow chart illustrating an example of a method 500 of outputting a notification regarding a size of a smart garment. The method 500 can be implemented by the server 310 (e.g., the garment application 350) or the smart garment 200 (e.g., the processor 105) of FIG. 1. The following description discusses implementation of the method 500 by the garment application 350, but it will be understood that the processor 105 can implement the method 500 using suitable configured computer program code.

At step 502, the garment application 350 can receive sensor data generated by at least a first portion of a plurality of sensors integrated into a smart garment, the sensor data indicating a level at which fabric of the smart garment is stretched when worn by a user. At step 504, the garment application 350 can determine, using a processor, based on the sensor data, at least one size change parameter indicating at least one change in a size of the user. At step 506, the garment application 350 can, based on the at least one size change parameter indicating the at least one change in the size of the user, determine whether a size of the smart garment is not suitable for the smart garment to be worn by the user. At step 508, the garment application 350 can, responsive to determining that size of the smart garment is not suitable for the smart garment to be worn by the user, output a notification indicating that the size of the smart garment is not suitable for the smart garment to be worn by the user. At step 510, the garment application 350 can, responsive to determining that size of the smart garment is not suitable for the garment to be worn by the user, output another notification indicating a garment size that is suitable for the user. At step 512, the garment application 350 can, responsive to determining that size of the smart garment is not suitable for the garment to be worn by the user, output another notification indicating a particular garment having a garment size that is suitable for the user.

FIG. 6 is a flow chart illustrating an example of a method 600 of outputting a notification regarding a risk of disease for a user. The method 600 can be implemented by the server 310 (e.g., the garment application 350) of FIG. 1.

At step 602, the garment application 350 can receive sensor data generated by at least a portion of a plurality of sensors integrated into a smart garment, the sensor data indicating at least one biometric parameter indicating a state of health of a user. At step 604, the garment application 350 can determine, based on the sensor data, a risk of disease for the user. At step 606, the garment application 350 can determine whether the risk of the disease for the user exceeds a threshold value. At step 608, the garment application 350 can, responsive to determining that the risk of the disease for the user exceeds the threshold value, output a notification indicating the risk of the disease for the user.

FIG. 7 is a flow chart illustrating an example of a method 700 of outputting a notification regarding a change in the state of health of a user. The method 700 can be implemented by the server 310 (e.g., the garment application 350) of FIG. 1.

At step 702, the garment application 350 can receive sensor data generated by at least a portion of the plurality of sensors integrated into the smart garment, the sensor data indicating at least one biometric parameter indicating a state of health of a user. At step 704, the garment application 350 can determine, based on the sensor data, at least one health change parameter indicating at least one change in the state of health of the user. At step 706, the garment application 350 can, based on the at least one health change parameter indicating the at least one change in the state of health of the user, determine whether the at least one change in the state of health of the user exceeds a threshold value. At step 708, the garment application 350 can, responsive to determining that the at least one change in the state of health of the user exceeds the threshold value, output a notification indicating that the at least one change in the state of health of the user exceeds the threshold value. At step 710, the garment application 350 can output another notification indicating a recommendation for the user to take at least one action to mitigate a health risk resulting from the change in the state of health of the user.

While the disclosure concludes with claims defining novel features, it is believed that the various features described herein will be better understood from a consideration of the description in conjunction with the drawings. The process(es), machine(s), manufacture(s) and any variations thereof described within this disclosure are provided for purposes of illustration. Any specific structural and functional details described are not to be interpreted as limiting, but merely as a basis for the claims and as a representative basis for teaching one skilled in the art to variously employ the features described in virtually any appropriately detailed structure. Further, the terms and phrases used within this disclosure are not intended to be limiting, but rather to provide an understandable description of the features described.

For purposes of simplicity and clarity of illustration, elements shown in the figures have not necessarily been drawn to scale. For example, the dimensions of some of the elements may be exaggerated relative to other elements for clarity. Further, where considered appropriate, reference numbers are repeated among the figures to indicate corresponding, analogous, or like features.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a," "an," and "the" are intended to include the plural forms as well, unless the context clearly indicates otherwise. It will be further understood that the terms "includes," "including," "comprises," and/or "comprising," when used in this disclosure, specify the presence of stated features, integers, steps, operations, elements, and/or components, but do not preclude the presence or addition of one or more other features, integers, steps, operations, elements, components, and/or groups thereof.

Reference throughout this disclosure to "one embodiment," "an embodiment," or similar language means that a particular feature, structure, or characteristic described in connection with the embodiment is included in at least one embodiment described within this disclosure. Thus, appearances of the phrases "in one embodiment," "in an embodiment," and similar language throughout this disclosure may, but do not necessarily, all refer to the same embodiment.

The term "plurality," as used herein, is defined as two or more than two. The term "another," as used herein, is defined as at least a second or more. The term "coupled," as used herein, is defined as connected, whether directly without any intervening elements or indirectly with one or more intervening elements, unless otherwise indicated. Two elements also can be coupled mechanically, electrically, or communicatively linked through a communication channel, pathway, network, or system. The term "and/or" as used herein refers to and encompasses any and all possible combinations of one or more of the associated listed items. It will also be understood that, although the terms first, second, etc. may be used herein to describe various elements, these elements should not be limited by these terms, as these terms are only used to distinguish one element from another unless stated otherwise or the context indicates otherwise.

The term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, comprising:
receiving first sensor data generated by at least a first portion of a plurality of sensors integrated into a smart garment, the first sensor data indicating a level at which fabric of the smart garment is stretched when worn by a user;
determining, using a processor, based on the first sensor data, at least one size change parameter indicating at least one change in a size of the user;
based on the at least one size change parameter indicating the at least one change in the size of the user, determining whether a size of the smart garment is not suitable for the smart garment to be worn by the user; and
responsive to determining that size of the smart garment is not suitable for the smart garment to be worn by the user, outputting a first notification indicating that the size of the smart garment is not suitable for the smart garment to be worn by the user.

2. The method of claim 1, further comprising:
responsive to determining that size of the smart garment is not suitable for the smart garment to be worn by the user, outputting a second notification indicating a garment size that is suitable for the user.

3. The method of claim 1, further comprising:
responsive to determining that size of the smart garment is not suitable for the smart garment to be worn by the user, outputting a second notification indicating a particular garment having a garment size that is suitable for the user.

4. The method of claim 1, further comprising:
receiving second sensor data generated by at least a second portion of the plurality of sensors integrated into the smart garment, the second sensor data indicating at least one biometric parameter indicating a state of health of the user;
determining, based on the second sensor data, a risk of disease for the user;
determining whether the risk of the disease for the user exceeds a threshold value; and
responsive to determining that the risk of the disease for the user exceeds the threshold value, outputting a second notification indicating the risk of the disease for the user.

5. The method of claim 1, further comprising:
receiving second sensor data generated by at least a second portion of the plurality of sensors integrated into the smart garment, the second sensor data indicating at least one biometric parameter indicating a state of health of the user;
determining, based on the second sensor data, at least one health change parameter indicating at least one change in the state of health of the user;
based on the at least one health change parameter indicating the at least one change in the state of health of the user, determining whether the at least one change in the state of health of the user exceeds a threshold value; and
responsive to determining that the at least one change in the state of health of the user exceeds the threshold value, outputting a second notification indicating that the at least one change in the state of health of the user exceeds the threshold value.

6. The method of claim 5, further comprising:
outputting a third notification indicating a recommendation for the user to take at least one action to mitigate a health risk resulting from the change in the state of health of the user.

7. The method of claim 5, wherein the biometric parameter is a parameter selected from a group consisting of a body temperature parameter, a heart rate parameter, a respiration rate parameter, a perspiration rate parameter and a blood pressure parameter.

8. A system, comprising:
a processor programmed to initiate executable operations comprising:
receiving first sensor data generated by at least a first portion of a plurality of sensors integrated into a smart garment, the first sensor data indicating a level at which fabric of the smart garment is stretched when worn by a user;

determining based on the first sensor data, at least one size change parameter indicating at least one change in a size of the user;

based on the at least one size change parameter indicating the at least one change in the size of the user, determining whether a size of the smart garment is not suitable for the smart garment to be worn by the user; and responsive to determining that size of the smart garment is not suitable for the smart garment to be worn by the user, outputting a first notification indicating that the size of the smart garment is not suitable for the smart garment to be worn by the user.

9. The system of claim 8, the executable operations further comprising:

responsive to determining that size of the smart garment is not suitable for the smart garment to be worn by the user, outputting a second notification indicating a garment size that is suitable for the user.

10. The system of claim 8, the executable operations further comprising:

responsive to determining that size of the smart garment is not suitable for the smart garment to be worn by the user, outputting a second notification indicating a particular garment having a garment size that is suitable for the user.

11. The system of claim 8, the executable operations further comprising:

receiving second sensor data generated by at least a second portion of the plurality of sensors integrated into the smart garment, the second sensor data indicating at least one biometric parameter indicating a state of health of the user;

determining, based on the second sensor data, a risk of disease for the user;

determining whether the risk of the disease for the user exceeds a threshold value; and responsive to determining that the risk of the disease for the user exceeds the threshold value, outputting a second notification indicating the risk of the disease for the user.

12. The system of claim 8, the executable operations further comprising:

receiving second sensor data generated by at least a second portion of the plurality of sensors integrated into the smart garment, the second sensor data indicating at least one biometric parameter indicating a state of health of the user;

determining, based on the second sensor data, at least one health change parameter indicating at least one change in the state of health of the user;

based on the at least one health change parameter indicating the at least one change in the state of health of the user, determining whether the at least one change in the state of health of the user exceeds a threshold value; and responsive to determining that the at least one change in the state of health of the user exceeds the threshold value, outputting a second notification indicating that the at least one change in the state of health of the user exceeds the threshold value.

13. The system of claim 12, the executable operations further comprising:

outputting a third notification indicating a recommendation for the user to take at least one action to mitigate a health risk resulting from the change in the state of health of the user.

14. The system of claim 12, wherein the biometric parameter is a parameter selected from a group consisting of a body temperature parameter, a heart rate parameter, a respiration rate parameter, a perspiration rate parameter and a blood pressure parameter.

15. A computer program product comprising a computer readable storage medium having program code stored thereon, the program code executable by a processor to perform a method comprising:

receiving, by the processor, first sensor data generated by at least a first portion of a plurality of sensors integrated into a smart garment, the first sensor data indicating a level at which fabric of the smart garment is stretched when worn by a user;

determining, by the processor, based on the first sensor data, at least one size change parameter indicating at least one change in a size of the user;

based on the at least one size change parameter indicating the at least one change in the size of the user, determining, by the processor, whether a size of the smart garment is not suitable for the smart garment to be worn by the user; and responsive to determining that size of the smart garment is not suitable for the smart garment to be worn by the user, outputting, by the processor, a first notification indicating that the size of the smart garment is not suitable for the smart garment to be worn by the user.

16. The computer program product of claim 15, the method further comprising:

responsive to determining that size of the smart garment is not suitable for the smart garment to be worn by the user, outputting a second notification indicating a garment size that is suitable for the user.

17. The computer program product of claim 15, the method further comprising:

responsive to determining that size of the smart garment is not suitable for the smart garment to be worn by the user, outputting a second notification indicating a particular garment having a garment size that is suitable for the user.

18. The computer program product of claim 15, the method further comprising:

receiving second sensor data generated by at least a second portion of the plurality of sensors integrated into the smart garment, the second sensor data indicating at least one biometric parameter indicating a state of health of the user;

determining, based on the second sensor data, a risk of disease for the user;

determining whether the risk of the disease for the user exceeds a threshold value; and responsive to determining that the risk of the disease for the user exceeds the threshold value, outputting a second notification indicating the risk of the disease for the user.

19. The computer program product of claim 15, the method further comprising:

receiving second sensor data generated by at least a second portion of the plurality of sensors integrated into the smart garment, the second sensor data indicating at least one biometric parameter indicating a state of health of the user;

determining, based on the second sensor data, at least one health change parameter indicating at least one change in the state of health of the user;

based on the at least one health change parameter indicating the at least one change in the state of health of the user, determining whether the at least one change in the state of health of the user exceeds a threshold value; and responsive to determining that the at least one change in the state of health of the user exceeds the threshold value, outputting a second notification indicating that the at least one change in the state of health of the user exceeds the threshold value.

20. The computer program product of claim 19, the method further comprising, further comprising:

outputting a third notification indicating a recommendation for the user to take at least one action to mitigate a health risk resulting from the change in the state of health of the user.

* * * * *